(12) United States Patent
Grajek et al.

(10) Patent No.: US 9,016,282 B2
(45) Date of Patent: Apr. 28, 2015

(54) STERILE IMAGING HEAD PROTECTION APPARATUS AND METHOD OF PROVIDING PROTECTION TO A RADIOLOGICAL IMAGING HEAD THEREWITH

(71) Applicants: Mark S. Grajek, Howell, MI (US);
Michael G. Howe, Fenton, MI (US);
Michael W. Czop, Fenton, MI (US)

(72) Inventors: Mark S. Grajek, Howell, MI (US);
Michael G. Howe, Fenton, MI (US);
Michael W. Czop, Fenton, MI (US)

(73) Assignee: Contour Fabricators, Inc., Fenton, MI (US)

(*) Notice: Subject to any disclaimer, the term of this patent is extended or adjusted under 35 U.S.C. 154(b) by 208 days.

(21) Appl. No.: 13/731,964

(22) Filed: Dec. 31, 2012

(65) Prior Publication Data

US 2013/0167845 A1 Jul. 4, 2013

Related U.S. Application Data

(60) Provisional application No. 61/581,677, filed on Dec. 30, 2011, provisional application No. 61/610,187, filed on Mar. 13, 2012.

(51) Int. Cl.
| | | |
|---|---|---|
| *A61F 5/37* | (2006.01) | |
| *A61B 6/00* | (2006.01) | |
| *A61B 19/08* | (2006.01) | |
| *A61B 19/12* | (2006.01) | |
| *A01K 39/012* | (2006.01) | |

(52) U.S. Cl.
CPC .............. *A61B 19/081* (2013.01); *A61B 6/00* (2013.01); *A61B 6/4423* (2013.01); *A61B 6/4441* (2013.01); *A61B 6/487* (2013.01); *A61B 19/088* (2013.01); *A61B 19/12* (2013.01); *A01K 39/012* (2013.01)

(58) Field of Classification Search
USPC .................................................. 128/849–856
See application file for complete search history.

(56) References Cited

U.S. PATENT DOCUMENTS

| | | | | |
|---|---|---|---|---|
| 8,286,637 B2* | 10/2012 | Kaska | ............ | 128/852 |
| 2001/0036245 A1* | 11/2001 | Kienzle et al. | ............ | 378/4 |
| 2005/0047734 A1* | 3/2005 | Borom | ............ | 385/98 |
| 2006/0076024 A1* | 4/2006 | Duarte | ............ | 128/849 |
| 2012/0006960 A1* | 1/2012 | Ahlman | ............ | 248/309.1 |
| 2012/0191107 A1* | 7/2012 | Tanner et al. | ............ | 606/130 |

* cited by examiner

*Primary Examiner* — Michael A. Brown
(74) *Attorney, Agent, or Firm* — John D. Wright; Dickinson Wright PLLC

(57) ABSTRACT

A sterile imaging head protective apparatus includes a radiolucent rigid sheet configured to cover an imaging head of an X-ray imaging machine and a sterile flexible drape attached to the radiolucent rigid sheet. The drape extends away from the radiolucent rigid sheet to an open free end. A member is provided adjacent the open end, wherein the member is operable to maintain the open end in abutment with a portion of the X-ray imaging machine.

29 Claims, 5 Drawing Sheets

FIG. 3
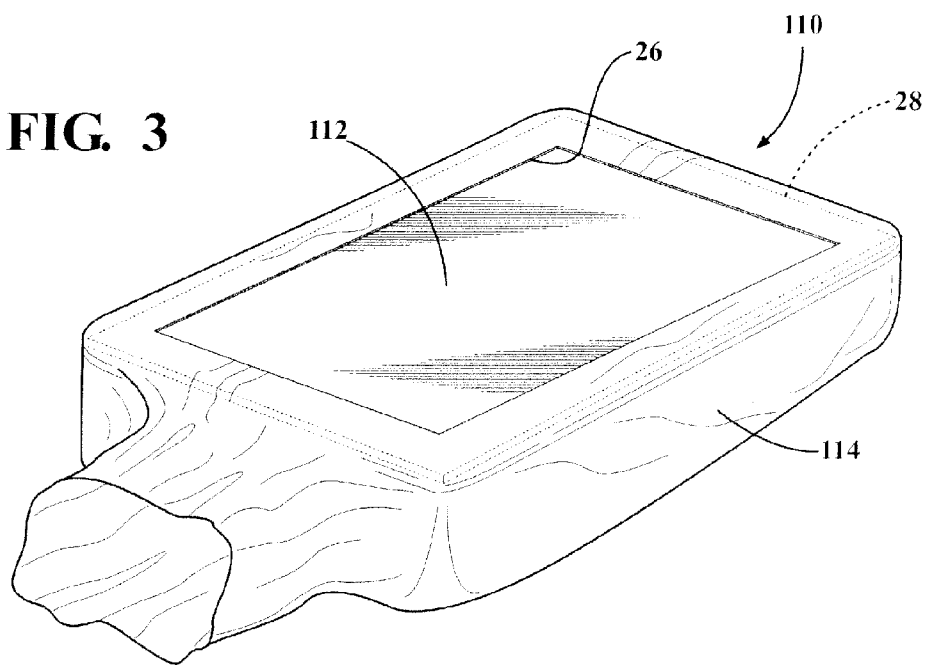
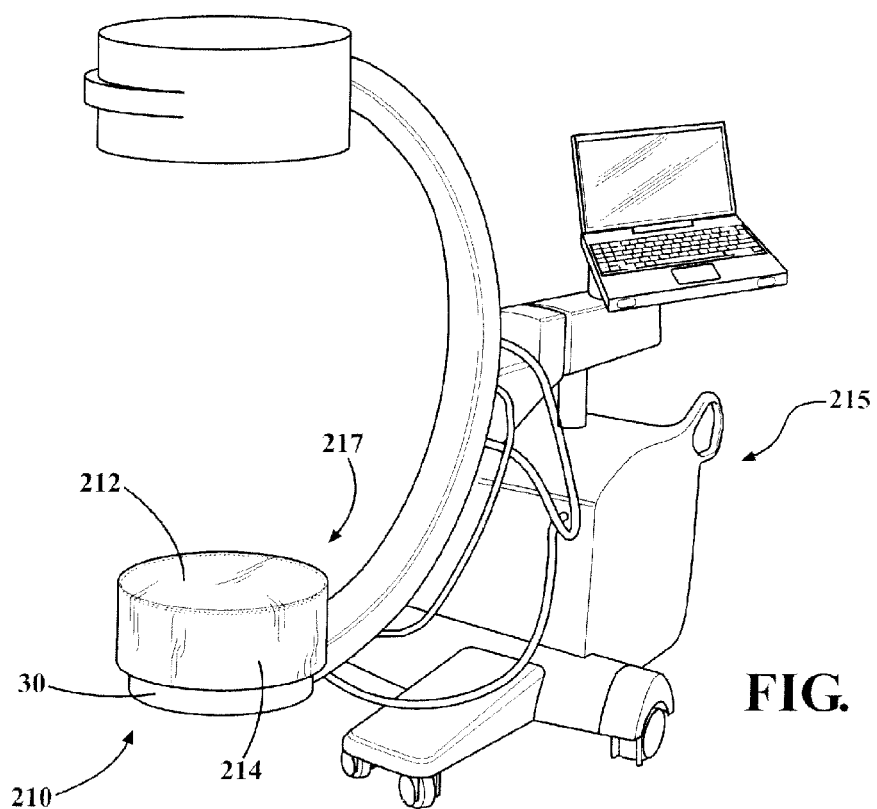
FIG. 4

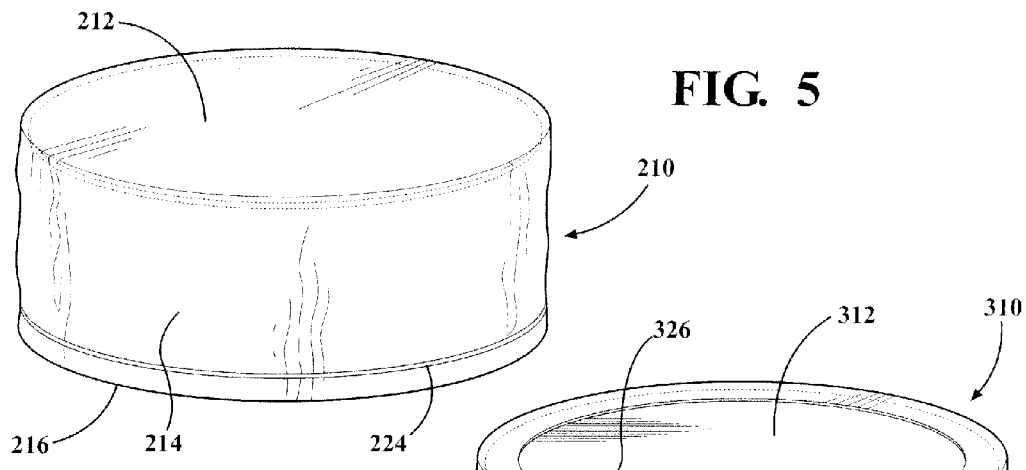
FIG. 5
FIG. 6
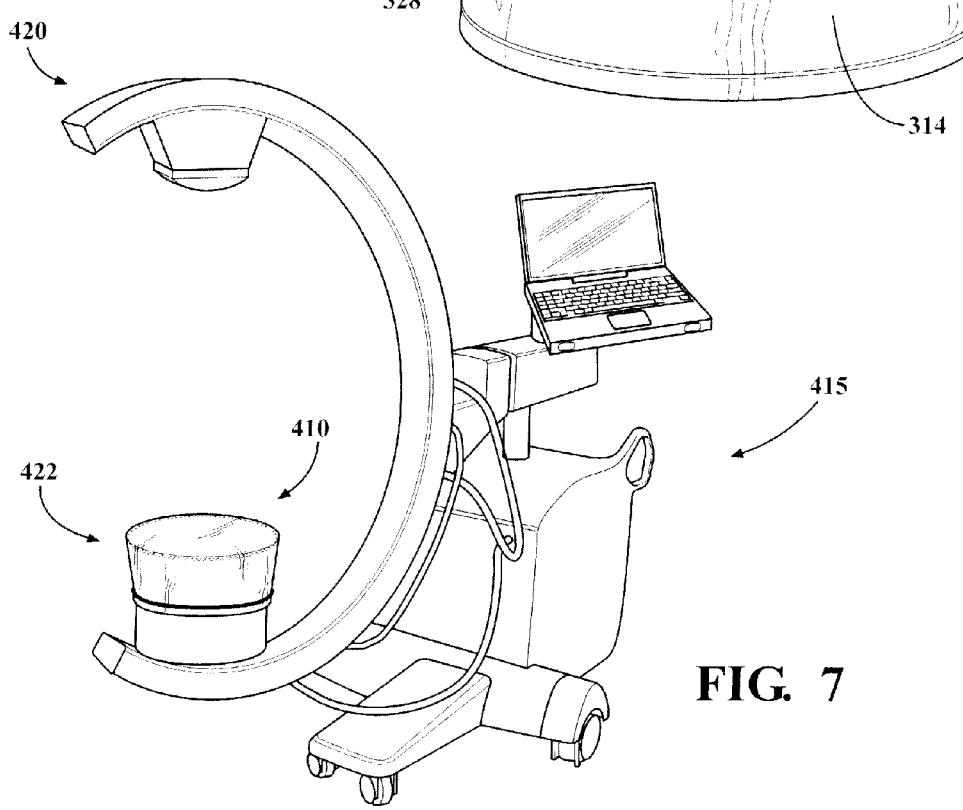
FIG. 7

STERILE IMAGING HEAD PROTECTION APPARATUS AND METHOD OF PROVIDING PROTECTION TO A RADIOLOGICAL IMAGING HEAD THEREWITH

CROSS-REFERENCE TO RELATED APPLICATION

This application claims the benefit of U.S. Provisional Application Ser. No. 61/581,677, filed Dec. 30, 2011, and also the benefit of U.S. Provisional Application Ser. No. 61/610,187, filed Mar. 13, 2012, which are incorporated herein by reference in their entirety.

BACKGROUND OF THE INVENTION

1. Technical Field

This invention relates generally to surgical apparatus, and more particularly to sterile protective apparatus used to cover imaging heads of radiological imaging equipment.

2. Related Art

The need to provide a sterile environment in a surgical theatre is directly associated with the known risk of infection that can be caused by bacteria, such as from a person or surgical equipment, in the surgical theatre. As such, it is known that in order to minimize the risk of infection during a surgical procedure, it is necessary to prevent the transfer of bacteria, such as via airborne lint or dust particles, fluids, or otherwise, within the surgical theatre. Although the risks of infection caused during surgery are known, it remains a challenge to minimize the risks associated with the onset of infection caused during surgery. Infections have been estimated to affect about 2 million patients annually and result, directly or indirectly, in an estimated 100,000 deaths. Aside from the loss of life, infections create an economic burden on hospitals. For example, some studies estimate that each bloodstream infection in a patient results in an average cost of about $27,000 to the hospital. As such, many states have passed laws detailing how hospitals treat patients in an effort to decrease the risk of infection to the patients.

In orthopedic surgeries it is common to take radiological images of various parts of the patient's body as the surgery is being performed. One common piece of radiological imaging equipment used to image the patient is a fluoroscopy system including a fluoroscope. The fluoroscopy system allows the physician to obtain real-time moving images of the internal structures of a patient through the use of the fluoroscope. In its simplest form, a fluoroscope consists of an X-ray emitter and fluorescent screen, between which, a portion of a patient is placed. Modern fluoroscopes couple the fluorescent screen to an X-ray intensifier or detector and a CCD video camera allowing the images to be recorded and played real-time on a monitor.

One common fluoroscopy system used to image the patient is a C-arm fluoroscopy unit. A C-arm fluoroscopy unit obtains its name from a C-shaped arm extending between opposite ends, with one end having an X-ray emitting head attached thereto and the opposite end having a X-ray imaging head attached thereto. Different types of X-ray imaging heads commonly used are known as flat detectors and image intensifiers. Regardless of the type of imaging head used, they typically have an outer flat imaging surface.

During some procedures, the physician may place a patient's limb directly on the flat imaging surface to facilitate performing the surgical procedure. This is particularly common in orthopedic procedures, such as on a hand or arm, for example. During these procedures, the physician needs to see, in real-time, the location of surgical instruments, such as Kirschner wires, commonly referred to as "K-wires", which are sterilized, sharpened, smooth stainless steel pins. K-wires come in different sizes and are used to hold bone fragments together (pin fixation) or to provide an anchor for skeletal traction. The pins are often driven into the bone through the skin (percutaneous pin fixation) using a power or hand drill. As such, when the patient's limb is positioned directly on the flat imaging surface, it is important for the physician to be extremely careful when positioning the K-wire to avoid causing damage to the underlying imaging surface, such as can occur if the K-wire is inadvertently driven through the patient's skin. Given the fact that, in many cases, the physician is using a good deal of force to position the K-wire, it is not unheard of for the K-wire to extend through the patient's skin and impinge the underlying image surface, thereby causing damage to the imaging surface, regardless of how much care the physician is using.

In addition to being careful to avoid damaging the imaging surface, it is particularly important to ensure the flat surface is sterile. Further yet, the flat imaging surface must remain uniformly radiolucent, which is a problem when using common protective apparatus in the form of bag-shaped sterile drapes to cover the flat, non-sterile imaging surface of the imaging head. When using a bag-shaped sterile drape, the drape is typically placed over the flat imaging surface to provide a sterile barrier about the imaging surface. Unfortunately, wrinkles typically form in the highly flexible sterile drape over the flat imaging surface, which in turn causes the resulting image produced by the imaging head to be distorted. As such, the surgeon, whom is reliant on the images produced by the imaging equipment to perform the surgery, is forced to work with less than clear images, thereby complicating the surgery process.

SUMMARY OF THE INVENTION

A sterile imaging head protective apparatus is provided. The apparatus includes a radiolucent rigid sheet configured to cover an imaging head of an X-ray imaging machine and a sterile flexible drape attached to the radiolucent rigid sheet. The drape extends away from the radiolucent rigid sheet to an open free end. Further, a member is provided adjacent the open end, wherein the member is operable to maintain the open end in abutment with a portion of the X-ray imaging machine.

In accordance with another aspect of the invention, the radiolucent rigid sheet has opposite planar sides with the sterile flexible drape being bonded to one of the opposite sides.

In accordance with another aspect of the invention, the sterile flexible drape is bonded to an entire flat surface of the rigid sheet in wrinkle-free fashion.

In accordance with another aspect of the invention, the sterile flexible drape has an opening and the radiolucent rigid sheet is bonded to the sterile flexible drape about the opening to close off the opening.

In accordance with another aspect of the invention, the member is an elastic band.

In accordance with another aspect of the invention, the protective apparatus includes a housing. The housing has an annular wall with a central through opening and a cavity configured to receive a portion of the fluoroscope imaging head. The radiolucent rigid sheet is fixed to the housing and closes off the central through opening.

In accordance with another aspect of the invention, the cavity has a planar counterbore surface spaced from a planar end surface in generally parallel relation to the planar end surface and a cylindrical inner surface configured for close receipt of the portion of the fluoroscope imaging head. The central through opening extends between the planar end surface and the planar counterbore surface.

In accordance with another aspect of the invention, the housing is compliant.

In accordance with another aspect of the invention, the housing is constructed of closed cell foam.

In accordance with another aspect of the invention, the radiolucent rigid sheet is carbon fiber.

In accordance with another aspect of the invention, the radiolucent rigid sheet is a polycarbonate resin thermoplastic.

In accordance with another aspect of the invention, the sterile flexible drape is attached to one of the housing and the planar sheet of rigid radiolucent material.

In accordance with another aspect of the invention, an imaging head protective apparatus includes a housing having an annular wall with central through opening depending from a planar end surface, with the housing having a cavity configured to receive a portion of an imaging head of a fluoroscope. Further, the apparatus includes a rigid radiolucent planar sheet fixed to the planar end surface to close off the central through opening.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 3 illustrates a schematic perspective view of a sterile imaging head protective apparatus constructed in accordance with another aspect of the invention for use with the C-arm radiological imaging machine of FIG. 1;

FIG. 4 is a perspective view of C-arm radiological imaging machine with a sterile imaging head protective apparatus constructed in accordance with another aspect of the invention disposed over an imaging head of the imaging machine;

FIG. 5 illustrates a schematic perspective view of the sterile imaging head protective apparatus of FIG. 4;

FIG. 6 illustrates a schematic perspective view of a sterile imaging head protective apparatus constructed in accordance with another aspect of the invention for use with the C-arm radiological imaging unit of FIG. 4;

FIG. 7 is a perspective view of C-arm radiological imaging machine having an imaging head with a sterile imaging head protective apparatus constructed in accordance with another aspect of the invention disposed over the imaging head;

DETAILED DESCRIPTION OF PRESENTLY PREFERRED EMBODIMENTS

Figure 1:
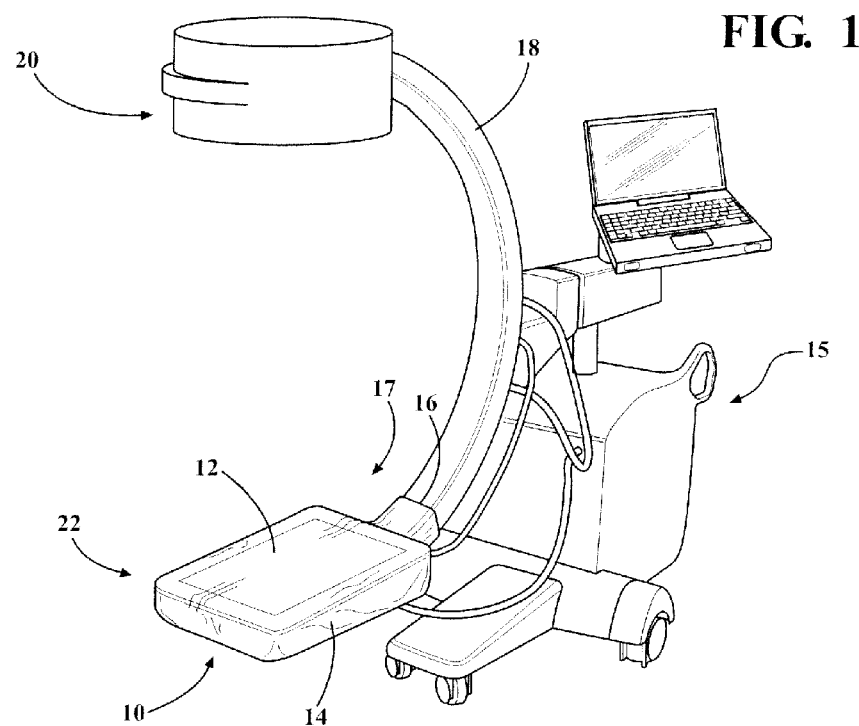
FIG. 1 is a perspective view of C-arm radiological imaging machine having an imaging head with a sterile imaging head protective apparatus constructed in accordance with one aspect of the invention disposed over the imaging head.

Referring in more detail to the drawings, FIG. 1 illustrates a sterile imaging head protective apparatus, referred to hereafter as protective apparatus 10, constructed in accordance with one aspect of the invention. The protective apparatus 10 includes a high impact resistant, radiolucent rigid sheet 12 of material, such as a polycarbonate resin thermoplastic, e.g. Lexan®, by way of example and without limitation, and a radiolucent sterile flexible drape 14, such as polyethylene, by way of example and without limitation, bonded to one another. The protective apparatus 10 provides and maintains a sterile outer surface about a portion of a C-arm type radiological imaging machine 15, and particularly about an imaging head of the imaging machine 15, wherein the imaging head can be provided as an image intensifier or a flat detector 17. The high impact resistant, rigid sheet 12 forms a surgical surface 19 that provides protection to the underlying surface of the imaging machine 15 from potentially damaging impact forces during the surgical procedure, such as from surgical instruments. In some procedures, the portion of the patient being imaged can rest directly on the surgical surface 19 without fear of causing damage to the imaging machine 15, even if surgical instruments were to impact the surface 15. The flexible drape 14 extends from the rigid sheet 12 to an open free end 16. The protective apparatus 10 is economical in construction, and thus, is well suited to be disposed after single use, and further provides a quick and easy mechanism in which to reliably ensure a sterile surgical theater is maintained throughout a surgical procedure, at least with regard to potential contamination stemming from the imaging machine 15, without having to sterilize the flat detector 17 of the imaging machine 15 prior to performing the procedure. Accordingly, the protective apparatus 10, in addition to performing its impact resistant, sterilization function, greatly reduces the potential for infection to a patient in an economical manner.

The protective apparatus 10 is constructed for particular use with the C-arm type, flat detector radiological imaging unit 15. The C-arm type radiological machine, also referred to as a C-arm fluoroscope or fluoroscopy machine, and referred to hereafter simply as imaging machine 15, is commonly used in surgical procedures that require images to be taken of the patient throughout the surgical procedure, such as an orthopedic procedure on the forearm or hand of the patient, by way of example and without limitation. The imaging machine 15, as the name implies, has an arcuate, generally C-shaped arm 18 that extends between a proximal X-ray emitting radiological imaging head, also referred to as upper imaging head 20, and the distal X-ray processing radiological imaging head, also referred to as lower imaging head 22. The lower imaging head 22 is represented, by way of example, as having the flat detector 17 attached thereto, on which the intended portion of the patient to be imaged rests.

Figure 2:
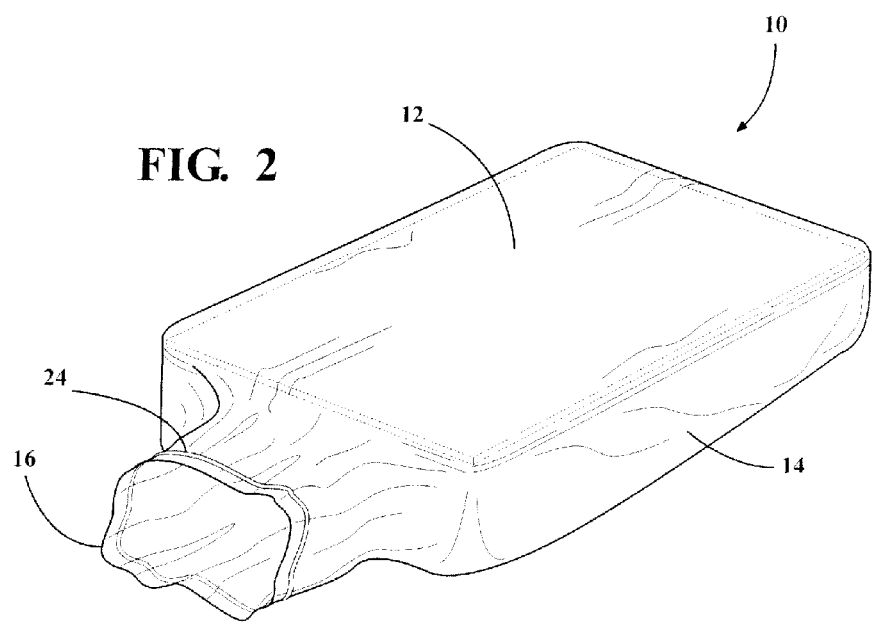
FIG. 2 illustrates a schematic perspective view of the sterile imaging head protective apparatus of FIG. 1.

The flexible drape 14 of the protective apparatus 10 is configured to cover a portion of the C-shaped arm 18 to provide sterility about the covered arm portion, while the planar rigid sheet 12 is configured to lay flat on the flat detector 17. Accordingly, the flexible drape 14 provides a portion of an enclosure constructed of a flexible, tear and puncture-resistant material, such as a clear radiolucent plastic material, for example, about the covered portion of the arm 18. Further, the planar radiolucent rigid sheet 12, with particular reference to the embodiment depicted in FIG. 2, facilitates providing the portion of the flexible drape 14 that extends and is bonded entirely thereover with a wrinkle-free surface through which the X-rays pass without being reflected or refracted in an unwanted manner. As such, the X-rays impinging the rigid sheet 12 and portion of the drape 14 bonded thereto are unimpeded as they pass through the flexible drape 14 and underlying rigid sheet 12. To provide the wrinkle-free surface, the flexible drape 14 is stretched taught and then bonded to the rigid sheet 12 while in its stretched, wrinkle-free state. As such, the X-ray image produced by the flat detector 17 is clear and unblemished, thereby providing the surgeon with an accurate portrayal of the portion of the patient being imaged. As mentioned, the flexible drape 14 extends completely over the underlying rigid sheet 12 and is bonded thereto, such as via any suitable radiolucent adhesive.

To facilitate maintaining the protective apparatus 10 in its intended fixed location relative to the imaging machine 15, the open free end 16 of the flexible drape 14 has an attachment member 24, such as a strap, tie cord, or elastic band, by way of example, extending adjacent the open free end 16. The attachment member 24 is configured to draw an end portion of the flexible drape 14 into contact with imagine machine 15, shown here as the C-arm 18, to releasably fix the open free end 16 to the C-arm 18, thereby ensuring the sterile imaging drape 10 remains fixed during use. Of course, upon completing the surgical procedure, the attachment member 24 is readily removable from its fixed engagement with the C-arm 18, thereby allowing the protective apparatus 10 to be removed from the imaging machine 15 and disposed.

As shown in FIG. 3, a protective apparatus 110 constructed in accordance with another aspect of the invention is shown, wherein the same reference numerals, offset by a factor of 100, are used to identify like features described above. The notable difference is with regard to the flexible drape 114, which instead of completely covering the rigid sheet 112, has an opening 26 bounded by an annular edge that is sized to be bonded about an outermost peripheral edge 28 of the rigid sheet 112. As such, the rigid sheet 112 is not completely covered by the flexible drape 114, and thus, the outer surface of the rigid sheet 112 provides a portion of the sterile coverage about the lower imaging head. Accordingly, a portion of the flexible drape 114 immediately adjacent the edge bounding the opening 26 overlies the rigid sheet 112 immediately adjacent the outermost peripheral edge 28 of the rigid sheet 112 and is bonded thereto via any suitable adhesive, as discussed above. Otherwise, the protective apparatus 110 is the same as discussed above with regard to the protective apparatus 10, and thus, is not discussed further.

As shown in FIG. 4, a protective apparatus 210 constructed in accordance with another aspect of the invention is shown, wherein the same reference numerals, offset by a factor of 200, are used to identify like features described above. One notable difference is with regard to the imaging machine 215 being used in combination with the protective apparatus 210. Rather, than the imaging head being a rectangular in configuration, the imaging head 217 is shown as being round, such as a round flat detector or image intensifier, with the imaging head 217 resting on a cylindrical housing 30. Given the imaging head 217 is configured differently, so too is the protective apparatus 210.

As shown in FIG. 5, the rigid sheet 212 is configured having a round outer peripheral edge 228 to accommodate the round shape of the imaging head 217. Further, the flexible drape 214 extends downwardly from the rigid sheet 212 and is configured to extend about the cylindrical housing 30. As in the previous embodiments, an attachment member 224 is provided adjacent an open free end 216 of the flexible drape 214 to facilitate releasably fixing the protective apparatus 210 in position. In this embodiment, the sterile flexible drape 214 extends completely over the underlying rigid sheet 212, thereby providing a sterile outer surface over the rigid sheet 212. In addition, as with the embodiment of FIG. 2, the portion of the flexible drape 214 covering the rigid sheet 212 is bonded in its entirety in wrinkle-free fashion to the rigid sheet 212 via any suitable radiolucent adhesive, thereby allowing a clear, non-distorted image to be taken via the imaging head 217.

As shown in FIG. 6, a protective apparatus 310 constructed in accordance with another aspect of the invention is shown, wherein the same reference numerals, offset by a factor of 300, are used to identify like features as described above. The notable difference between the protective apparatus 310 and the protective apparatus 210 is with regard to the flexible drape 314, which instead of completely covering the rigid sheet 312, has an opening 326 that is sized to be bonded about an outermost peripheral edge 328 of the rigid sheet 312. As such, the rigid sheet 312 is not completely covered by the flexible drape 314, and thus, the outer surface of the rigid sheet 312 provides a portion of the sterile coverage about the imagining head 317. Accordingly, a portion of the flexible drape 314 overlies the rigid sheet 312 immediately adjacent the outermost peripheral edge 328 and is bonded thereto via any suitable adhesive. Otherwise, the protective apparatus 310 is the same as discussed above with regard to the protective apparatus 210, and thus, is not discussed further.

Figure 8:
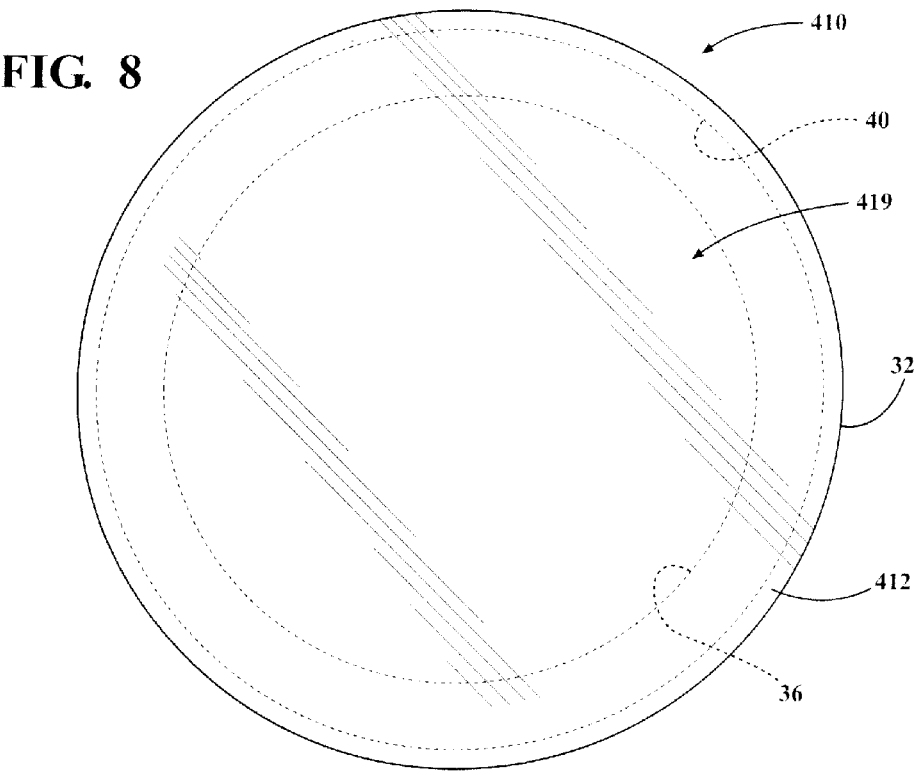
FIG. 8 is a plan view of the sterile imaging head protective apparatus of FIG. 7.
Figure 9:
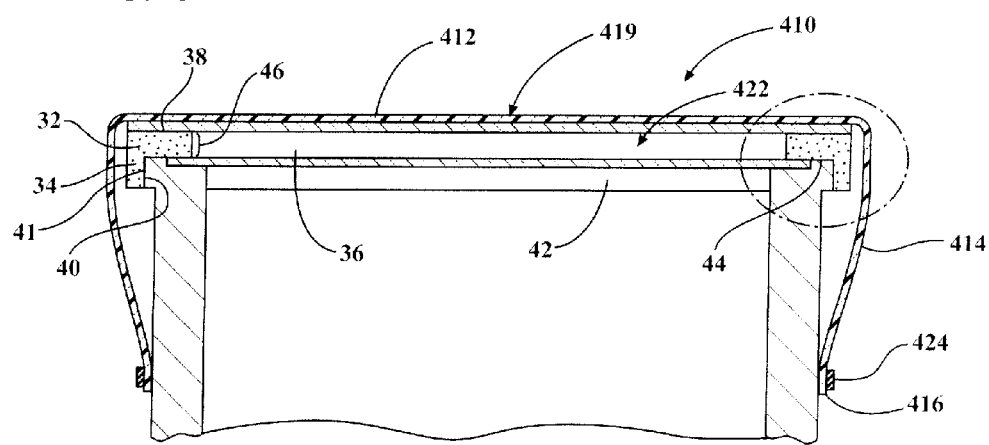
FIG. 9 is a cross-sectional view of the sterile imaging head protective apparatus of FIG. 8 shown disposed on a lower imaging head of the imaging unit of FIG. 7.
Figure 10:
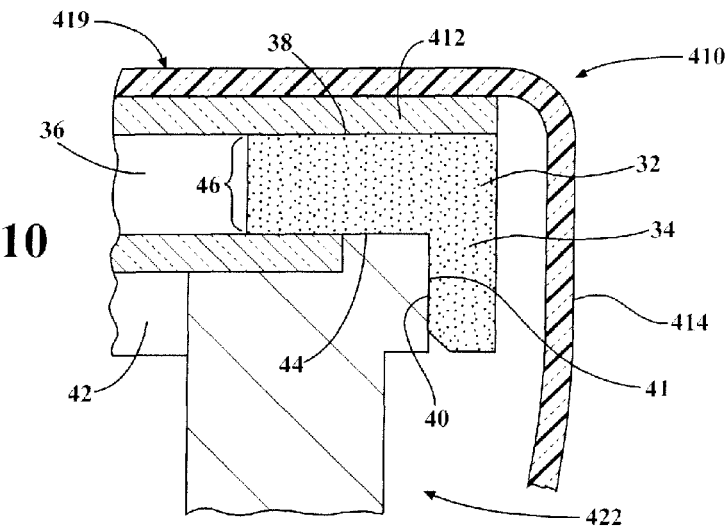
FIG. 10 is an enlarged partial view of the encircled area 10 of FIG. 9.

In accordance with another aspect of the invention, FIG. 7, wherein the same reference numerals, offset by a factor of 400, are used to identify like features as described above, illustrates an imaging machine 415 similar to that discussed above, however, rather than a lower imaging head 422 being a flat detector, the lower imaging head 422 is provided as an image intensifier, which can either be round or rectilinear. In FIGS. 8 and 9, a sterile protective cover assembly, also referred to as imaging head protective apparatus or simply as protective apparatus 410, constructed in accordance with another aspect of the invention is shown. The protective apparatus 410, similarly as described for the previously discussed embodiments, is used in combination with the imaging machine 415 during a surgical procedure to both provide sterilization and to protect the lower imaging head 422 from potentially damaging impact forces during the surgical procedure, such as from surgical instruments. The protective apparatus 410 allows images to be produced by the image intensifier of the lower imaging head 422 without causing the images to become distorted; it provides a rigid, impact resistant sterile surgical surface 419 upon which a patient's limb can be placed and operated on, while at the same time providing protection to the underlying image intensifier 422 by providing a tough, durable, radiolucent barrier over the image intensifier 422, thereby preventing a surgical instrument or other objects, e.g. K-wire, from inadvertently impacting and damaging the image intensifier 422.

The protective apparatus 410 includes a housing 32 constructed of a compliant material, such as an open or closed cell foam, for example. The housing 32 has an annular wall 34 with central through opening 36 depending from a planar end surface 38. The housing further includes an inner surface 40 bounding a cavity 42 configured to receive at least a portion of the image intensifier 422 in a close fit therein. With the housing 32 being formed of a compliant material, the inner surface 40 and an outer surface 41 of the image intensifier 422 can have an interference fit, or it could be a line-to-line fit or even a slightly loose fit, though it is contemplated that a snug fit would be preferred to minimize any potential relative movement from occurring between the protective apparatus 410 and the image intensifier 422. The cavity 42, in addition to the generally cylindrical inner surface 40, has a planar counterbore base or surface 44 spaced from the planar end surface 38 in generally parallel relation to thereto, with the central through opening 36 extending between the planar end surface 38 and the planar counterbore surface 44. The counterbore surface 44 acts as a stop surface while disposing the protective apparatus 410 on the image intensifier 422, thereby providing an air gap or space 46 extending between the image intensifier 422 and the surgical surface 419.

The surgical surface 419 is constructed from a planar sheet 412 of rigid, high impact resistant radiolucent material, such as from a sheet of carbon fiber material, for example. The sheet 412 is fixed to the planar end surface 38, such as via any suitable adhesive or bond joint, and closes off the central through opening 36. The thickness of the sheet 412 is selected, such as between about ⅛-¼", for example, to provide a durable, impenetrable surface to ordinary forces that may be encountered from a surgical instrument, such as while performing surgery on the limb of the patient thereon. As such, the underlying imaging head 422 is provided with a high degree of protection against impact.

The protective apparatus 410 can further include a flexible, tear resistant sterile drape 414 to facilitate maintaining sterility in the surgical theatre. The sterile drape 414 is preferably attached to the housing 32 and/or the rigid sheet 412, such as discussed above. The drape 414 extends downwardly from the rigid sheet 412 circumferentially about the wall 34 and beyond the wall 34 to an open free end 416. The free end 416 is configured to generally conform about the image intensifier 422, and can have an attachment member 424, e.g. elastic band or other fixation member fixed thereto to bring the free end 416 of the drape 414 into a close abutting fit with an outer surface of the lower imaging head 422. The drape 414 can be provided as a bag-shaped member having a bottom, closed end surface configured to conform closely with the surgical surface 419 in a free state, or the closed end surface could be fixed in wrinkle free fashion to the surgical surface 419 similarly as discussed above with regard to the apparatus 10. Otherwise, the drape 414 can be provided with an opening having a periphery configured to be fixed to an outermost periphery of the surgical surface 419, such as via an adhesive or bond joint, for example, as discussed above with regard to the apparatus 110.

Figure 11:
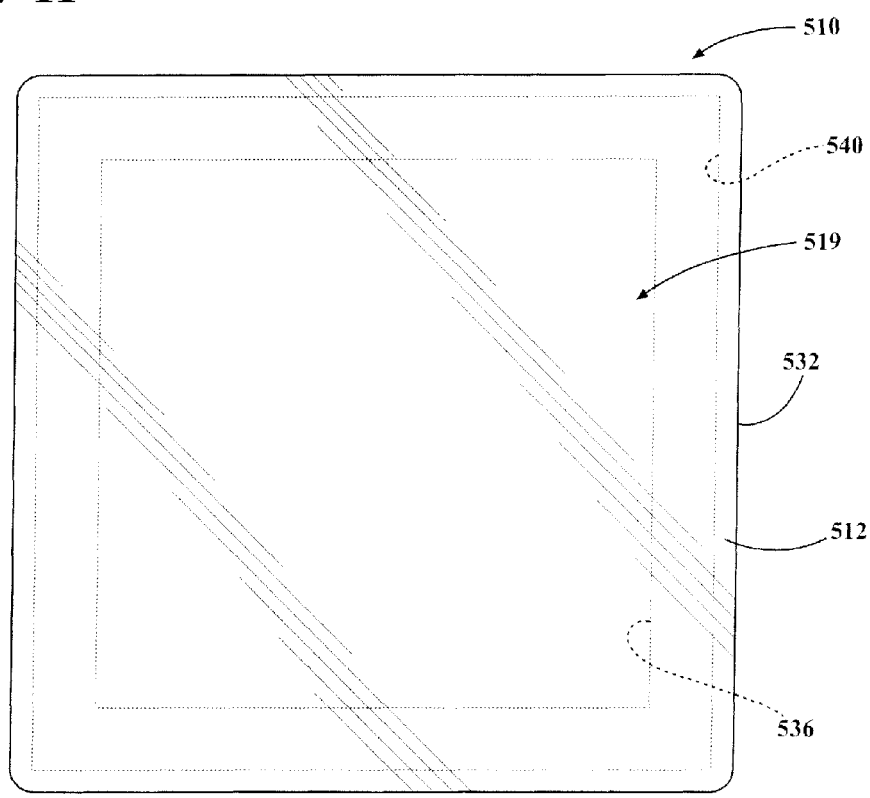
FIG. 11 is a view similar to FIG. 8 of a sterile imaging head protective apparatus constructed in accordance with another aspect of the invention.

In FIG. 11, a protective apparatus 510 constructed in accordance with another aspect of the invention is shown, wherein the same reference numerals, offset by a factor of 500, are used to identify like features as described above. The protective apparatus 510 is similar to that discussed above with reference to FIGS. 7-10, including having a housing 532 with a rigid, radiolucent planar sheet 512 providing a sterile surgical surface 519 lying thereover; however, rather than being round, the protective apparatus 510 is rectangular, and thus, the housing 532 has a rectangular inner surface 540 bounding a rectangular through opening 536 sized for receipt over a rectangular imaging head. Otherwise, the protective apparatus 510 is the same as discussed above with regard to the protective apparatus 410, and thus, is not discussed further.

Obviously, many modifications and variations of the present invention are possible in light of the above teachings. It is, therefore, to be understood that within the scope of the appended claims, the invention may be practiced otherwise than as specifically described.

What is claimed is:

1. A sterile imaging head protective apparatus, comprising:
a radiolucent rigid sheet configured to cover an imaging head of an X-ray imaging machine;
a sterile flexible drape attached to said radiolucent rigid sheet and extending away from said radiolucent rigid sheet to an open free end; and
a member adjacent said open end, said member being operable to maintain said open end in abutment with a portion of the X-ray imaging machine.

2. The sterile imaging head protective apparatus of claim 1 wherein said sterile flexible drape is radiolucent.

3. The sterile imaging head protective apparatus of claim 2 wherein said radiolucent rigid sheet has opposite planar sides, said sterile flexible drape being bonded to one of said opposite sides.

4. The sterile imaging head protective apparatus of claim 3 wherein said sterile flexible drape is bonded to an entire surface of said one side.

5. The sterile imaging head protective apparatus of claim 3 wherein said sterile flexible drape has an opening, said radiolucent rigid sheet being bonded to said sterile flexible drape about said opening and closing off said opening.

6. The sterile imaging head protective apparatus of claim 1 wherein said member is an elastic band.

7. The sterile imaging head protective apparatus of claim 1 further including a housing having an annular wall with central through opening depending from a planar end surface and having a cavity configured to receive a portion of the imaging head, wherein said radiolucent rigid sheet is fixed to said planar end surface and closes off said central through opening.

8. The sterile imaging head protective apparatus of claim 7 wherein said cavity has a planar counterbore surface spaced from said planar end surface in generally parallel relation to said planar end surface and a cylindrical inner surface configured for close receipt of the portion of the imaging head, said central through opening extending between said planar end surface and said planar counterbore surface.

9. The sterile imaging head protective apparatus of claim 8 wherein said counterbore surface is configured to abut an end surface of the imaging head.

10. The sterile imaging head protective apparatus of claim 7 wherein said housing is compliant.

11. The sterile imaging head protective apparatus of claim 10 wherein said housing is constructed of closed cell foam.

12. The sterile imaging head protective apparatus of claim 1 wherein said radiolucent rigid sheet is carbon fiber.

13. The sterile imaging head protective apparatus of claim 7 wherein said sterile flexible drape is attached to one of said housing and said planar sheet of rigid radiolucent material.

14. A sterile imaging head protective apparatus, comprising:
a housing having an annular wall with central through opening depending from a planar end surface and having a cavity configured to receive a portion of an imaging head of an X-ray imaging machine; and
a rigid radiolucent planar sheet fixed to said planar end surface and closing off said central through opening.

15. The sterile imaging head protective apparatus of claim 14 wherein said cavity has a planar counterbore surface spaced from said planar end surface in generally parallel relation to said planar end surface and a cylindrical inner surface configured for close receipt of the portion of the imaging head, said central through opening extending between said planar end surface and said planar counterbore surface.

16. The sterile imaging head protective apparatus of claim 15 wherein said counterbore surface is configured to abut an end surface of the imaging head.

17. The sterile imaging head protective apparatus of claim 14 wherein said housing is compliant.

18. The sterile imaging head protective apparatus of claim 17 wherein said housing is constructed of closed cell foam.

19. The sterile imaging head protective apparatus of claim 14 wherein said rigid radiolucent planar sheet is carbon fiber.

20. The sterile imaging head protective apparatus of claim 14 further comprising a sterile drape attached to one of said housing and said rigid radiolucent planar sheet.

21. The sterile imaging head protective apparatus of claim 20 where said sterile drape has an elastic band at a free end, said elastic band being configured to bring said drape into abutment with a surface of the imaging head.

22. The sterile imaging head protective apparatus of claim 20 wherein said sterile drape is bonded to said rigid radiolucent planar sheet.

23. A method of providing sterility and impact resistant protection to an imaging head of a C-arm type radiological machine, comprising:
   covering the imaging head with a radiolucent rigid sheet;
   extending a sterile flexible drape from the radiolucent rigid sheet; and
   drawing an end portion of the sterile flexible drape into contact with a portion of the C-arm type radiological machine to releasably fix the sterile flexible drape and radiolucent rigid sheet to the radiological machine.

24. The method of claim 23 further including fixing the radiolucent rigid sheet to a compliant housing and sizing a cavity of the housing for a close fit on the imaging head.

25. The method of claim 24 further including forming an air gap between the imaging head a portion of the radiolucent rigid sheet.

26. The method of claim 25 further including bonding the sterile flexible drape to the radiolucent rigid sheet and extending the sterile flexible drape from the radiolucent rigid sheet beyond the compliant housing to an open free end.

27. The method of claim 23 further including bonding the sterile flexible drape to the radiolucent rigid sheet.

28. The method of claim 27 further including forming an opening in the sterile flexible drape and bonding an annular edge bound the opening to the radiolucent rigid sheet.

29. The method of claim 27 further including bonding a portion of the sterile drape to completely cover the radiolucent rigid sheet in wrinkle-free fashion.

\* \* \* \* \*